United States Patent
Marowsky et al.

(10) Patent No.: US 6,710,870 B1
(45) Date of Patent: Mar. 23, 2004

(54) METHOD AND DEVICE FOR MEASURING LUMINESCENCE

(75) Inventors: Gerd Marowsky, Göttingen (DE); Dieter Neuschaefer, Muttenz (CH); Michael Pawlak, Laufenburg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/601,484

(22) PCT Filed: Feb. 3, 1999

(86) PCT No.: PCT/EP99/00701

§ 371 (c)(1),
(2), (4) Date: Aug. 3, 2000

(87) PCT Pub. No.: WO99/40415

PCT Pub. Date: Aug. 12, 1999

(30) Foreign Application Priority Data

Feb. 5, 1998 (CH) .............................. 278/98

(51) Int. Cl.[7] .................................. G01J 3/30
(52) U.S. Cl. ...................... 356/317; 356/311
(58) Field of Search .................. 356/311, 317

(56) References Cited

U.S. PATENT DOCUMENTS

| | | | | |
|---|---|---|---|---|
| 4,945,245 A | * | 7/1990 | Levin | 250/461.2 |
| 5,192,510 A | * | 3/1993 | Zoha et al. | 422/82.05 |
| 5,677,196 A | * | 10/1997 | Herron et al. | 436/518 |
| 6,198,869 B1 | * | 3/2001 | Kraus et al. | 385/129 |
| 6,208,791 B1 | * | 3/2001 | Bischel et al. | 385/129 |

FOREIGN PATENT DOCUMENTS

| | | |
|---|---|---|
| EP | 0 244 394 | 11/1987 |
| EP | 0 725 270 | 8/1996 |
| EP | 0 793 090 | 9/1997 |
| WO | 95/33197 | 12/1995 |
| WO | 95/33198 | 12/1995 |
| WO | 96/35940 | 11/1996 |

OTHER PUBLICATIONS

Sensors and Actuators B 38–39 (1997) 300–304 Lifetime-based Capillary Wavegide Sensor Instrumentation, D. Kieslinger et al., pp. 96–102, 1997.

* cited by examiner

Primary Examiner—Rodney Fuller
(74) Attorney, Agent, or Firm—Wenderoth, Lind & Ponack, L.L.P.

(57) ABSTRACT

A method exites and determines a luminescence in an analyte sample which is located in contact with the waveguiding layer of an optical layer waveguide. The luminescence is generated by non-evanescent excitation in the volume of the analyte sample. Luminescence radiation generated in the immediate proximity of the surface of the waveguiding layer is conducted to a measuring device and determined after penetrating the waveguiding layer.

10 Claims, 2 Drawing Sheets

METHOD AND DEVICE FOR MEASURING LUMINESCENCE

BACKGROUND OF THE INVENTION

1. Field of the Invention

The invention relates to a method for exciting and determining a luminescence of an analyte which is located in contact with a surface of a waveguiding layer of a layer waveguide. In a case of which, a luminescence is generated in a non-evanescent way in the volume of the analyte which leads to an optical measuring device from the immediate proximity on the surface of the waveguiding layer luminescence radiation which has penetrated into the waveguiding layer of the layer waveguide, preferably via at least one outcoupling element for the luminescence radiation. Then, the optical measuring device measures the luminescence light, for example, optoelectronically. The invention also relates to a measuring device for carrying out the method, and to a sensor platform.

2. Description of the Related Art

In affinity sensor technology, biochemical detection elements are immobilized on a waveguide surface either directly or via an adhesion promoter layer, for the purpose of specifically detecting an analyte in a sample, which can consist of a complex mixture of substances, and for the purpose of binding the analyte molecules on the surface of the wave guide, in the region of the depth of penetration of the evanescent field. In order to detect the, analyte, the sample in solution is brought into contact with detection elements immobilized on the waveguide surface, either in stop and flow or in throughflow.

Planar waveguides have recently been developed in the field, in particular, of biochemical analysis, for the purpose of generating and detecting evanescently excited radiation. In the evanescent field, there is generated a luminescence in contact with an analyte sample, for example, fluorescence, whose measurement permits a qualitative or quantitative determination of substances even in very low concentrations. The evanescently excited radiation emerging isotropically into space is determined optoelectronically by means of suitable measuring devices such as, for example, photodiodes, photomultipliers or CCD cameras. This method is disclosed, for example, in WO 95/33197. It is also possible for the fraction of the evanescently excited radiation coupled back into the waveguide to be coupled out via a diffractive optical element, for example, a grating, and measured. This method is described, for example, in WO 95133198. For the purpose of simultaneously or sequentially carrying out multiple measurements, arrays have become known in which at least two waveguides are arranged on a sensor platform which are driven separately with the aid of excitation light—see, for example, WO 96135940.

The known measuring methods place high requirements on the positioning accuracy of the excitation light with reference to the incoupling elements in order to achieve an adequate light incoupling and thus sensitivity. The use of adjusting components is therefore mandatory, and this complicates the technical design and is evident, in particular, in the case of the construction of arrays.

In addition, one is limited to the use of essentially coherent light in order to coordinate the positioning with the constants of the incoupling elements and such as, for example, diffractive gratings.

For classic, highly multimodal waveguides, such as, for example, multimode capillaries, multimode glass fibers or multimode glass platelets, the problem of high positioning requirements for coupling in the excitation light can be circumvented by applying the so-called "luminescence concentration principle" as described, for example, in Sensors and Actuators B 38 to 39 (1997), pages 96 to 102 and pages 300 to 304. However, here use is made of optical waveguides which comprise the substrate itself (without an additional more highly refractive layer), which is located in an environment with a low refractive index, and in the case of which waveguides a geometrical shape permits total reflection. It is described that the luminescence light from the emission sources applied to the substrate surface, such as, a polymer membrane with an embedded indicator dye, is collected over a large solid angle and then guided in the glass substrate to a detector located on an end face of the waveguide. Such indicator dyes are typically used in high, for example, millimolar, concentrations. Such thick glass substrates used as multimodal waveguides are not suitable for measuring very low detection concentrations.

SUMMARY OF THE INVENTION

It has now been found, surprisingly, that even in the case of optical layer waveguides comprising a transparent substrate and a highly refractive waveguiding layer it is possible to apply the principle of the "luminescence collector", and thus the problems associated with the coupling in of the excitation light are completely avoided when the excitation radiation is directed without the use of incoupling elements at least partially directly onto the volume of the analyte sample in order to generate the luminescence, for example, in a reflected-light or transmission arrangement. The luminescence radiation generated in the analyte sample in the immediate proximity of the surface of the waveguiding layer is, surprisingly, coupled into the waveguiding layer to a measurable extent and can, for example, be detected optoelectronically at the end face of optical fibers or planar waveguides, or via outcoupling elements in the case of planar waveguides. Luminescence generated in the further analyte volume is, surprisingly, virtually not coupled into the waveguiding layer, as a result of which interfering luminescence radiation generated in the a analyte is excluded, and a virtually background-free measurement is permitted which has high spatial selectivity, high efficiency and high sensitivity.

Layer structures composed of a transparent substrate such as, for example, glass, quartz or plastics such as polycarbonate, with a lower refractive index than the highly refractive waveguiding layer, applied to the surface, within a refractive index of for example at least 1.8 are as layer waveguides within the scope of the invention. The thickness of the waveguiding layer is preferably selected such that it can guide only a single or only a few (for example, up to 1) discrete modes of light of a specific wavelength. The layer waveguides are denoted below as waveguides for short.

It has been found, surprisingly, that not only luminescence excited by optical radiation, but even luminescence generated by other mechanisms such as, for example, chemiluminescence, triboluminescence, bioluminescence or electroluminescence, can be measured optoelectronically with the aid of layer waveguides, and this makes available a new method for highly sensitive determination of such luminescence radiation.

Direct irradiation of the analyte sample located in contact with the waveguide surface offers the following advantages, for example:

very sensitive detection with tithe aid of a configuration corresponding to conventional epifluorescence excitation;

use of coherent or noncoherent radiation sources, since the luminescence is not generated by the evanescent field of excitation radiation guided in a waveguiding layer, but luminescence radiation generated in the immediate proximity of the surface of the waveguiding layer of a waveguide is measured;

distinction between volumetric luminescence and luminescence radiation generated in the immediate optical proximity, which permits a measurement in turbid analyte samples such as, for example, blood, serum or reaction mixtures;

low requirements on the positioning accuracy of the excitation light;

low technical outlay in the use of sensor platforms with at least two separate waveguiding regions (sensor fields) for simultaneous measurements;

virtually background-free detection by means of a detection position completely separate in space from the site of excitation;

technically simple implementation of array formats such as, for example, a microtiter plate format, with adaptation to standardized sizes;

economic, cost-effective production even of compact forms of sensor systems, since requirements are placed on optomechanical adjusting devices;

use of cost-effective, freely selectable and commercial light sources, the wavelength region being set, if appropriate, by filters, use of excitation light with a wavelength of <450 nm, and possibility of excitation even with the aid of UV light;

use of sensor platforms with open cutouts in the nl to $\mu$l regions for holding samples;

use of layer waveguides; and low energy density of the excitation radiation, accompanied by gentle treatment of the analyte samples.

DETAILED DESCRIPTION OF THE INVENTION

A first object of the invention is a method for exciting and determining a luminescence in an analyte sample which is located in contact with a waveguiding layer of an optical layer waveguide, which is defined in that the luminescence is generated by non-evanescent excitation in the volume of the analyte sample. The luminescence radiation generated in the immediate proximity of the surface of the waveguiding layer is conducted to the measuring device and determined after penetrating the waveguiding layer.

In the immediate proximity of the surface of the waveguiding layer (denoted below as immediate optical proximity) means, for example, a distance of at most approximately one wavelength of a luminescence light, preferably of at most a half wavelength and, with particular preference, of at most approximately a quarter wavelength from the surface of the waveguiding layer.

The luminescence, for example, a fluorescence, can be excited in various ways. It is possible to arrange in the region of the sample holder electrodes with the aid of which the luminescence is excited by the application of an electric field. A chemiluminescence can be generated in the analyte sample by means of combining suitable chemicals. The excitation of luminescence is preferably performed optically by the direct (without incoupling element) non-evanescent irradiation of the analyte sample with the aid of light of suitable wavelengths. The wavelength region can reach, for example, from the shortwave UV to the near IR, preferably from 200 to 2000 nm, more preferably from 250 to 1400 nm and, with particular preference, 250 to 1000 nm. An evanescent luminescence excitation with the aid of UV light and the use of planar waveguides with incoupling elements is possible only to a limited extent, since grating periods of below 300 nm for coupling in the UV radiation can be produced only at great expense and, moreover, UV radiation is very strongly damped in the waveguide. The method according to the invention surprisingly permits, on the one hand, the use of UV light and, on the other hand, the use of the characteristic luminescence of molecules, which are to be determined by means of UV irradiation of the analyte sample with the result that if appropriate, there is no need to use luminophor labels such as, for example, fluorophor labels.

It is possible to use both coherent and noncoherent radiation, and thus any desired light source, for example, a polychromatic one. The radiation can be focused with the aid of lenses or mirrors and/or filters can be used to set narrower wavelength regions. It is also possible to use polarized radiation. Suitable radiation sources are, for example, lasers, diode lasers and white light from light-emitting diodes or incandescent or filament lamps such as, for example, halogen or mercury-vapor lamps.

Optical layer waveguides are known in abundance and some are commercially available. For the method according to the invention, these can have different geometrical shapes, for example, optical fibers, cylindrical bodies or planar waveguides. The substrate material with a low refractive index can be selected from organic glasses (for example, polycarbonate) or inorganic glasses (glasses, quartz, $SiO_2$) and the waveguiding layer with a higher refractive index can be selected from plastics or metal oxides such as $Ta_2O_5$, $TiO_2$, $ZnO$, $HfO_2$, $ZrT_2$ or $Nb_2O_5$. Preference is given to waveguides with very thin waveguiding layers and a high refractive index in which only a few (for example 1 to 3) modes are conducted.

The thickness of the waveguiding layer can be approximately 50 nm to 2000 mm, preferably 80 nm to 400 nm, and very particularly from 100 to 200 nm. The optimum selection of the layer thickness is a function of the wavelength of the luminescence to be detected. It is preferably 50 nm up to a wavelength, particularly preferably from 50 nm up to a half wavelength, and very particularly preferably from 50 nm up to a quarter wavelength. At the same time, waveguiding layers are preferred to have a high as possible refractive index, that is to say preferably of at least 1.8, particularly preferably of at least 2.0 and very particularly preferably of at least 2.2. As a result of these parameter values, the optical near field directly at the surface of the waveguide is particularly strong and falls away particularly steeply with distance from the waveguide surface, and this leads to a very effective and spatially highly specific (that is to say, limited essentially to a few 100 nm from the surface) coupling of the luminescence into the waveguide.

Planar waveguides are provided with at least one outcoupling element for the luminescence radiation, for example, prisms or, preferably, diffractive elements.

Diffractive elements are understood to be outcoupling elements for light radiation. Use is frequency made of gratings which can be produced in different ways. It is widespread to produce gratings with the aid of photolithographic etching techniques. Furthermore, such gratings can be arranged in the transparent substrates and/or the waveguiding layer, and be impressed during shaping or subsequently. It is also possible for such gratings to be produced by means of ablative methods (laser irradiation). Other production methods are holographic recordings, or incorporation of ions by ion bombardment. The adaptation of grating parameters such as modulation transfer factor, ratio of land to groove and grating period to the wavelengths of the luminescence radiation for an optimized outcoupling efficiency are known; The thickness of the waveguiding layer can be 100 to 200 nm. The modulation transfer factor can be 5 to 100 nm, preferably 5 to 60 nm. The ratio of the modulation transfer factor of the thickness of the waveguiding layer is preferably less than 0.5. The period of the diffractive element (diffraction grating) can be from 200 to 1000 nm, for example.

Planar waveguides are known and are commercially available. They can have one or more mutually opposite diffractive elements for coupling out the excited luminescence radiation. The diffractive elements are preferably of monodiffractive design for the purpose of detecting luminescence of a single emission band. If luminescences of different wavelengths are to be detected, the diffractive elements are preferably of multidiffractive design. Multidiffractive grating couplers for use in measuring arrangements for detecting changes in the so-called effective refractive index in the evanescent field of a waveguide are likewise known and described, for example, in WO 95114225.

The individual lines of the diffractive elements can be straight or bent and also be of circular design in the case of only one existing diffractive element. If two diffractive elements are present, they can have the same grating constants, or different grating constants in order, for example, to direct the emitted luminescence light onto only one detector.

When the method according to the invention is being carried out, it is possible for a part or the whole volume of an analyte sample to be irradiated. The irradiation can be performed at an oblique angle, and preferably at a right angle to the waveguide surface. Depending on the use of optical fibers or planar waveguides, the measuring devices can be of different design and differently arranged.

In the case of the use of optical glass fibers, the method can be carried out such that the analytes are put into a measuring cell, for example, a cuvette, which can be designed as a closed cell or a flow cell. One or more glass fibers can be connected to a closure designed as a measuring head. The luminescence radiation guided to the end face of a glass fiber can then be measured optoelectronically. The irradiation of the analyte sample can be performed through the cuvette, and if appropriate, via an optical window. A part or the entire volume of an analyte sample can be irradiated. Irradiation can be performed at an oblique angle, preferably at a right angle to the glass fiber.

In the case of the use of planar waveguides, the arrangement of the radiation source, detection elements and sample is chiefly determined by the planarity of the waveguide.

In the case of planar waveguides, the element provided for holding an analyte, for example, a sample container in the form of a depression, is generally integrated on the waveguiding layer in contact with the waveguide. The sample containers can in this case have a volume of 0.1 nl to 100 $\mu$l, and preferably 10 nl to 10 $\mu$l. The sample containers can be open or closed at the top, with flow cells being involved in a case of the second named embodiment. The planar waveguides with applied sample containers are denoted below as sensor platforms.

The optical coupling elements, preferably designed as diffractive gratings, can be arranged inside and outside the sample containers. This yields different requirements for the properties of the second layer which is brought into contact with the waveguiding layer and in which the sample containers are produced. If the optical coupling elements are situated inside the sample containers, there are no further special requirements for the optical properties and their arrangement with reference to the position and alignment of diffractive gratings as optical coupling elements. In order to reduce possible optical crosstalk between neighboring sensor fields on a sensor platform, the second layer in this case is preferably absorbent at the luminescence wavelength to be detected.

If the optical coupling elements are located outside the sample containers and are thereby completely covered by the second layer, which has the advantage of ensuring stable outcoupling conditions, the second layer, in contact with the waveguide surface, must be transparent, in the case of the wavelength of the luminescence wavelength to be detected, at least to the depth of penetration of the evanescent field of guided luminescence light, that is to say at least up to at least one wavelength, and preferably up to at least 10 micrometers. In this arrangement, the boundary of the sample containers is advantageously located at a distance of from 1 micrometer up to a centimeter, preferably from 5 micrometers up to 5 mm, from the diffractive element or elements. The second layer, in contact with the wavelength surface, preferably has in this region as low a surface roughness as possible of, for example, less than 2 nm RMS, and makes contact with the waveguide surface without a gap in order to avoid increasing scattering losses in the guided luminescence light.

The orientation of the grating lines in the case of diffractive gratings as coupling elements is preferably essentially in the same direction as the course of the border of the sample containers. In the case of closed, for example, circular or elliptic, diffractive elements, the sample containers are preferably located at their center. In the case of two or more interrupted diffractive elements, the sample containers are preferably located in the middle between opposite diffractive elements.

The sensor platforms can be designed such that they comprise only one waveguide with diffractive elements. However, the sensor platforms can comprise a one dimensional or two-dimensional arrangement of at least two waveguides with diffractive elements, it being possible to arrange an arbitrary number of waveguides with diffractive elements one behind the other and/or next to one another, for example, up to 100 or more, advantageously 2 to 50 per row and/or line. These arrangements can be rectangular or round, for example. Particularly if the sample containers are open at the top, the external dimensions of the sensor platforms, and the arrangement of the sample containers can advantageously correspond to the shape of known and possibly standardized microtiter platforms. The number of the sample containers on a sensor platform is preferably being an integral multiple of 96 as the traditional standard for microtiter plates.

In this connection, sample containers can be dispensed with when use is made of one-dimensional or two-dimensional arrangements of at least two waveguides with diffractive elements (arrays), and the analyte sample to be investigated can be applied directly to the measuring regions (sensor fields) of the waveguiding layer. It is possible to use known methods for this purpose, such as, for example, carrying out the application using micropipettes or inkjet printers.

The production of sensor platforms with open sample containers can be performed using methods known per se, for example, photolithograhically by means of photopolymerizable layers which are applied to the waveguiding layer, possibly via an adhesion-promoting interlayer, the latter having to be transparent at least in the case of the luminescence wavelength to be detected if the diffractive elements are located outside the sample containers. Another possibility consists of applying vacuum vapor deposition methods with a mask, with the aid of which a multiplicity of materials can be applied, chiefly oxides such as, for example, $SiO_2$ or $Al_2O_3$. A further possibility consists of applying ablation methods such as, for example, etching methods, with the aid of a mask and/or laser irradiation. The methods can also be combined.

In the case of sensor platforms with one-dimensional or two-dimensional arrangements of more than one sensor elements which are equipped with diffractive elements for coupling out luminescence and formed in a continuous waveguiding layer, it can be expedient to interrupt the waveguidance between neighboring sensor elements by applying layers which are absorbing at least in the case of the luminescence wavelength to be detected. The application of the absorbing layers can be done, for example, by spreading or printing. Furthermore, this can be performed by vapor deposition of metal oxides, using vacuum coating methods, or with the use of light-absorbing materials such as, for example, intermediate cutouts filled with carbon or blackened materials in the layer containing the sample containers, in contact with the waveguide surface. Interference owing to crosstalk of excitation and/or luminescence light is thereby suppressed.

The individual sensor elements can also be separated by an interruption of the waveguiding layer around the sensor elements, in order to avoid interference through crosstalk. The interruption can be achieved by simply removing the waveguiding layer in a narrow region about the elements, for example, mechanically by means of scratching, by means of etching methods or irradiation with a laser. Furthermore, the interruption of the waveguiding layer can already be achieved using masks during the application of the waveguiding layer.

If the diffractive elements are situated outside the sample containers, it is also possible to prefabricate cover layers composed of materials transparent to the luminescence radiation and, if appropriate, also to the excitation radiation at least in the region of the depth of penetration of the evanescent field of guided luminescence light, preferably up to at least ten micrometers, possibly with, as described above, light-absorbing regions outside the region of the sensor fields and the associated diffractive elements, and then to connect them to the waveguiding layer, as the case may be with the aid of an adhesion promoter for which the same requirements for transparency or absorption properties are valid as a function of the position with reference to the diffractive elements.

In carrying out the method according to the invention with planar waveguides, it is possible to irradiate the analyte sample from outside, that is to say upstream of or between the outcoupling elements directly at an inclined or preferably right angle, with reference to the waveguide, (a) from above through the analyte sample if the direction of the waveguiding layer and through the waveguide or (b) preferably front below through the waveguide, from the direction of the substrate material. It can be advantageous in this case to use mirrors on the side of the sensor platform opposite the direction of irradiation to produce a two fold passage of the excitation light through the sample if an increase in scattered light falling onto the detection units is avoided by the shaping of the optical excitation geometry. In the case of sample containers of the sensor platform which are closed at the top, and of irradiation of the excitation light from the direction of the substrate material, it is possible, for example, for the top side of the cutouts to be mirror-coated. In the case of irradiation of the excitation light from above through the analyte sample, the outside of the substrate material can be mirror-coated in the region of the sample containers and between the diffractive elements.

The simultaneous irradiation of one-dimensional or two-dimensional arrays of sensor elements can be performed, for example, using a light beam expanded over a large area (for simultaneous irradiation of a two-dimensional array), elliptically or in the shape of a slit (for simultaneous irradiation of the one-dimensional array). However, this is associated with the production of different irradiation intensities on the various sensor elements, something which is to be ascribed, for example, in the case of the use of lasers or laser diodes, essentially to their Gaussian beam profile and has to be taken into account in evaluating the generated luminescence signals. A more uniform intensity of irradiation on the various sensor elements can be achieved, for example, by reproducing a single excitation light beam, preferably from a laser or a laser diode, by means of a Dammann grating or a microlens array. A very uniform intensity of the individual excitation beams can be achieved by means of a Dammann grating for generating a one-dimensional or two-dimensional array of individual excitation beams from a single light source. If a numerically very large array of sensor elements, for example, 100 or more sensor elements, is to be illuminated simultaneously, the intensity of the individual beams can become very slight given the use of compact, and thus generally relatively low-powered (with reference to the excitation intensities) excitation light sources, and this can worsen the achievable detection limits of the method. This can be countered, on the one hand, by using more highly powered, but in general also larger excitation light sources. If, at the same time, it is desired to miniaturize the measuring arrangement, the use of arrays of miniaturized laser diodes as excitation light sources is preferred. Arrays of edge-emitting laser diodes such as are currently commercially available in a spectral region above approximately 600 nm are suitable, for example. Very particularly preferred, in particular for use with sensor arrays of very high density, are so-called surface-emitting Vertical Cavity Surface Emitting Laser diodes (VCSELs) as described, for example, in MINAST-News 2/1997, pages 13 and 14. These laser diode arrays are distinguished by a multiplicity of very favorable properties for use in accordance with the invention:

very high conversion efficiency of the laser current into emitted laser light and a relatively low generation of heat associated therewith, which permits a high packing density on a platform, in particular in the case of additional use of cooling elements on which demands which are correspondingly relatively low are placed;

very small dimensions of the emitting laser aperture in the lower micrometer region, which permits the measuring arrangement to be miniaturized to an extreme extent together with the vertical arrangement of the laser cavity on the substrate and with the possible high packing density;

very low variation in the emission intensities of VCSELs produced on a single wafer, and the possibility of selective driving given an appropriate design of the control electronics;

very small aperture angles of the emission cone in the case of the use of small exit openings and monomodal emission up to milliwatt intensities given the use of low drive currents, and low production costs per individual VCSEL owing to simultaneous production of a large number of VCSELs on a single wafer.

The fraction, generated in the near field of the waveguide, of the luminescence radiation excited in the analyte volume and coupled at least partially into the waveguide is guided in the latter and coupled out at the optical coupling elements. The coupled-out luminescence light can then be directed onto optoelectronic detection elements and measured.

Since, in addition to the dependence on the thickness of the waveguiding layer, the strength of the evanescent field of guided modes is also dependent on their polarization (transverse electric, TE, or transverse magnetic, TM), something which is also valid for the mechanism, subject to similar physical laws, of the coupling in (the penetration) of luminescence generated in the near field of the waveguide, for the purpose of increasing the sensitivity, that is to say, for the purpose of achieving deeper detection limits. It can be advantageous to detect the luminescence coupled out at the diffractive elements in a polarization-selective fashion. This is facilitated by virtue of the fact that the coupling-out of luminescence light of the same wavelength but different polarization (TE or TM) is performed at clearly different angles. It can, in particular, be advantageous in the case of coupling out spectrally broadband luminescence, that is to say, luminescence coupled out under a wide cone, to make use of additionally polarization-selective optical components in the beam path of the coupled-out luminescence between the diffractive outcoupling elements and the optoelectronic detection units.

Further details on the design of a measuring arrangement and on the selection of light sources, optical elements for guiding and discriminating the excitation radiation and luminescence radiation, as well as detection units for determining the luminescence radiation are described in detail in WO 95/33197 and WO 95/33198.

In using measuring cells in which the sample liquid comes into contact with the diffractive coupling elements, the problem arises that the conditions for coupling in the excitation light can change through molecular adsorption or binding onto the incoupling elements. In addition, excitation of unbound luminescent or fluorescent molecules by means of the fraction of the excitation light which is not coupled partially into the waveguide but enters the solution without diffraction as zero order excites in the depth of the sample background luminescence or background fluorescence which can be coupled partially into the waveguide via the optical coupling elements and impair the accuracy and sensitivity of the determination of the analyte.

A flow cell made from silicone rubber and applied to an optical waveguide with incoupling and outcoupling gratings is described in Analytical Chemistry, volume 62, No. 18 (1990), pages 2012 to 2017. The incoupling and outcoupling elements are situated in the region of the sample flow channel. This arrangement is used to measure variations in the light absorption and in the refractive index, without a selective interaction with specific detection elements on the waveguide surface. Adsorption phenomena on the surface are not taken into consideration for the analyte, a dye solution in the case of the absorption-dependent measurement, or liquids of different refractive indexes in the case of measurement as a function of refractive index. In the case of these very insensitive measurements, the changes to be expected in the effective refractive index for a mode guided in the waveguide can be neglected even in the case of adsorption of a monolayer of molecules by comparison with the strong variations in the refractive index of the solutions supplied, by contrast, with the interference to be expected in the case of the very much more sensitive method of determining the luminescence generated in the evanescent field. In the case of the measuring method which is a function of the refractive index and based on the change in the incoupling or outcoupling angle, the contact between the sample and the coupling elements is, of course, even a necessity for generating the measuring signal. Because of this configuration, with incoupling and outcoupling elements located inside the sample flow channel, the sample cell has a task only of sealing against escape of liquid without any further demands on optical properties of the material.

It has now been found, surprisingly, that it is possible to overcome the problems with sensor platforms when the layer provided for holding the samples covers the outcoupling elements at least in the region of the guided luminescence radiation, and is transparent to this radiation in the region of the bearing surface.

A further subject matter of the invention is a sensor platform composed of a planar optical layer waveguide, comprising a transparent substrate and a waveguiding layer, the waveguide having at least an outcoupling element for coupling out excitation radiation, and on whose waveguiding layer there is located a further tightly sealing layer, which has, at least in a subregion of the excitation radiation, a cutout open at the top, or a cutout which is closed at the top and connected via an inflow channel and outflow channel, for an analytical sample whose depth corresponds at least to the depth of penetration of the evanescent field of the luminescence light guided in the waveguide. The layer consists of a material which, at least on the bearing surface at least in the depth of penetration of the evanescent field of the luminescence light guided in the waveguide, is transparent to this luminescence light, and the outcoupling element or the outcoupling elements being completely covered by the material of the layer at least in the outcoupling region of the luminescence radiation.

The depth of the cutouts is preferably at least 1 $\mu$m, and with particular preference, at least 10 $\mu$m.

The statements and preferences previously made, including the one-dimensional and two-dimensional arrangements, hold for the waveguide.

The layer forming a cutout is transparent to electromagnetic radiation in the region of the luminescence wavelength, at least on the bearing surface. The material can be (organic glasses) such as, for example, polyesters, polycarbonates, polyacrylates, polymethacrylates or photopolymers. The layer is preferably formed from an elastomer. Particularly suitable are elastomers of polysiloxanes such as, for polydimethylsiloxanes, which are soft and flexible, as well as frequently self-adhesive materials. The materials for the layer are known and are commercially available in part.

The layer with at least one cutout can be produced by means of conventional shaping processes, for example, casting and pressing processes, or by means of grinding, punching and milling processes from appropriately pre-shaped semi-finished products. The layer can also consist of photopolymerizable substances which can be applied directly to the waveguiding layer by means of lithographic methods. Furthermore, the layer can consist of essentially inorganic materials such as Si or $SiO_2$ in which the sample containers are produced by means of etching methods. These materials are transparent in the region of the contact surface with luminescence light which is to be guided, at least up to the depth of penetration of the evanescent field of guided luminescence light, preferably up to a depth of at least 1 μm, and with very particular preference up to a depth of at least 10 μm, at least in the case of the luminescence wavelength.

With very smooth surfaces (surface roughness in the nanometer range or below), the self adhesion can lead through adhesion to tight seals in the case of stiff materials. Elastomers are generally self-adhesive. A possible slight surface roughness is also very desirable in order to suppress light scattering. In these cases, the layer is preferably produced as a separate body and applied with a tightly sealing contact to the waveguide, on whose surface there can be located immobilized detection elements, possibly on an additional thin (that is to say <100 nm) adhesion promoter layer.

The layer can consist of a single material which is transparent, at least for the luminescence wavelength of the analyte sample, and free from luminescence, or else be present as a two-ply layer whose first layer, which is brought into contact with the waveguide surface, is transparent at the luminescence wavelength of the analyte and is free from luminescence, while the adjoining cover layer is then preferably designed to absorb radiation. In this case, the thickness of the first layer, in contact with the waveguide surface, comprises at least the detector penetration of the evanescent field of guided luminescence light that is to say, approximately one wavelength. This first layer is preferably 0.8 μm to 10 mm, and more preferably 0.01 mm to 10 mm thick.

In an advantageous refinement, jumps in refractive index on the waveguiding layer along the propagation path of the luminescence light, which is to be guided up to the optical outcoupling elements, are minimized in the bearing layer. This can be performed by rounding the boundary of the cutout on the bearing surface in a fashion perpendicular to the waveguiding layer. A rounded transition perpendicular to the surface of the waveguide, at the boundaries of the cutouts, means that a right angle is avoided. The rounding can, for example, be a part of a circular, parabolic or hyperbolic curve. In the case of soft and flexible materials for the layer, the rounding is formed automatically in the course of being pressed onto the waveguide. The rounding can, however, also be preformed by the shaping process. Jumps in refractive index can also be minimized if the cutout is possibly continuously tapered in the direction of the propagation of the luminescence light. Another possibility consists of selecting the material of the layer forming the cutout to have a refractive index close to or equal to the refractive index of the analyte sample.

If a sensor platform contains a multiplicity of sensor elements and sample containers, it can be advantageous to provide light absorbing materials, for example, dyes, pigments, carbon black, metal oxides or metals for the purpose of suppressing scattered radiation and/or optical crosstalk between neighboring sensor elements along the cutouts. These materials can be applied in additional cutouts, provided therefor, along the edges of the sample containers, outside the region of the optical outcoupling elements, belonging to the sensor elements, on the surface of the waveguiding layer. Flat configurations, which can be produced simply by means of spreading or vapor deposition methods are expedient. The sensor platform can be shaped, for example, so as to provide damping material which absorbs radiation, evanescently excited in the spectral region, between the layer and the waveguide on both sides of the waveguide or of each cutout, so as to apply the damping material two-dimensionally as an immersion, or so as to provide damping cutouts which can be filled with damping material. If continuous waveguiding layers with more than one diffractive element are present, it is likewise expedient to separate the elements by means of absorbing materials. The sensor platform can also be configured such that the sensor elements are interrupted by removing a narrow region of the waveguide around the elements.

The sensor platform according to the invention can be provided in various embodiments, a distinction being made between embodiments with an open cutout (embodiment A) and a closed cutout (embodiment B, flow cells).

Embodiment A

The open cutouts can have any desired shape. The contact surfaces with the waveguide can, for example, be square, rectangular, round or ellipsoid. The shape of devices according to the invention can correspond to, for example, the shape of known microtiter plates. The geometrical arrangement of the cutouts is arbitrary per se, with two-dimensional arrangements being preferred. Devices and preferences illustrated and described for embodiment B can also be used in essence for embodiment A.

Embodiment B

In a sensor platform according to the invention for generating excited luminescence radiation, which has at least one outcoupling element for coupling out luminescence, excited in the near field of the waveguide and coupled into the waveguide, of excited radiation from the waveguide, it is expedient that the layer constructed as a flow cell also covers each outcoupling element. In a relevant development, it is provided that the cutout is arranged entirely next to or between each outcoupling element, such that each outcoupling element is free from sample material. This has the advantage that constant coupling conditions uninfluenced by the sample material prevail, during outcoupling of luminescence radiation guided in the waveguide.

Provided in the developments are a plurality of cutouts which can lead to interruption of the wave guidance between regions, assigned to the different sensor fields, of the sensor platforms. Apart from the optical coupling elements belonging to the sensor fields, it is expedient for this purpose to make provisions, in this portion of the intermediate regions of the cutouts complementary to the sensor fields, for material which is absorbed, for example, from the ultraviolet to the infrared spectral regions, in order to suppress crosstalk of radiation fractions between the cutouts. This can be performed, for example, by an absorbing layer which is applied between the flow cell and the waveguide. In another exemplary embodiment, damping cutouts which can be filled with a radiation-absorbing liquid are introduced for this purpose into the flow cell and are open toward the same surface side as the cutouts.

It is expedient, furthermore, for use in routine analytical operation that the layer in contact with the waveguide consists of a flexible material which tightly seals the at least one cutout when applied to the waveguide. As a result, in the case of cutouts closed at the top, it is possible without further aids such as seals to conduct sample material without leakage through a flow cell by placing the flow cell onto the waveguide.

A further subject of the invention is a device for measuring luminescence generated by excitation radiation in an analyte sample, comprising a) an optical layer waveguide with a transparent substrate and a waveguiding layer;
b) an analyte sample which is located in contact with the waveguiding layer;
c) an electric or optical energy source which is arranged such that the electrodes of the electric energy source are located in direct contact with the analyte sample, or the excitation radiation of the optical energy source is directed directly onto the analyte sample at an inclined or right angle, or a reservoir containing a chemical which excites a chemiluminescence in contact with the analyte sample; and
d) an optoelectronic detection unit for measuring the luminescence radiation generated by the action of an electric field or excitation radiation.

The waveguides a) are preferably planar waveguides which have at least one outcoupling element for coupling out luminescence radiation, preferably diffractive elements, and corresponding sensor platforms.

The energy source c) is preferably a light source and, as the case may be, focusing lenses, optical filters or both, whose excitation radiation is guided at an inclined or right angle either from above through the analyte sample and the waveguide, or from below through the waveguide and the analyte sample, in each case outside the outcoupling element or elements.

Otherwise, the previously presented preferences and embodiments hold for the device according to the invention. Further details on optical waveguides, optical elements for focusing, filters and guidance of excitation and luminescence light, as well as detection units for the excited radiation are described in WO 95/33197 and WO 95/33198.

The method according to the invention, and the device are suitable in general for determining luminescence light which is generated in the optical near field of a waveguide, for example, luminescence radiation generated chemically, electrically or, preferably, optically. Optical excitation is applied particularly in affinity sensor technology, in which the binding of the target molecules on their corresponding detection elements is detected using suitable fluorophores and by immobilizing one of the affinity partners. In this case, the immobilized affinity partners can be arranged both in an isolated fashion and embedded in larger functional structures up to whole cells. Examples of such analyses are human diagnosis, animal diagnosis, plant diagnosis, biochemical analysis, the investigation of reaction mixtures for process control, and environmental analysis. The analyte samples are preferably liquid, and measurements are possible without difficulty even in turbid solutions. The analyte samples can be, for example, egg yolk, blood, serum, plasma, liquids from internal organs (for example, the lymph system), plant extracts, soil extracts, water samples or synthetic liquors of biochemical processes. This method renders possible, for example, the qualitative or quantitative (after calibration) determination of antibodies and antigens, receptors or their ligands, oligonucleotides, DNA strands or RNA strands, DNA analogs or RNA analogs, enzymes, enzyme substrates, enzyme cofactors or inhibitors, lectins or carbohydrates. The method is also suitable for affinity screening in searching for and developing pharmaceutical or agrochemical active substances, for analysis in combinatorial chemistry, for and genotyping/phenotyping and mutation analyses of proteins and DNA strands or RNA strands.

Figure 1:
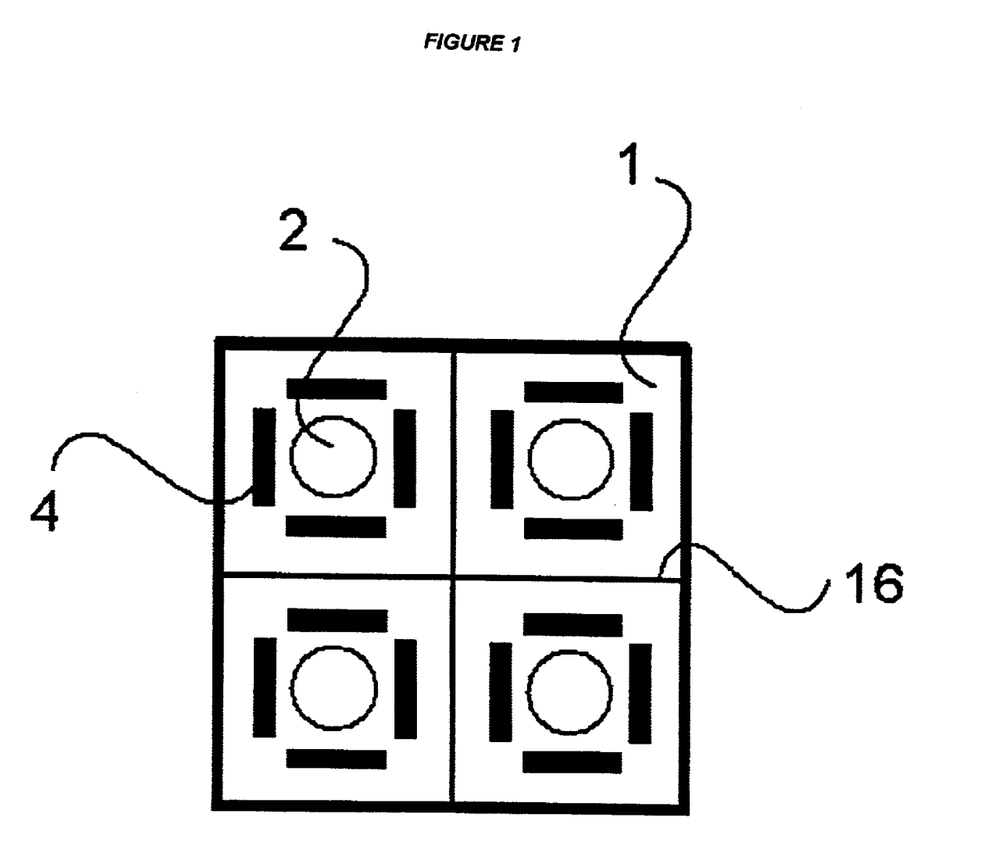
FIG. 1 illustrates a sensor platform.

FIG. 1 illustrates a sensor platform 1, designed as a microtiter plate, with four sensor fields. Here, 2 are cutouts for holding an analyte sample 3, which are located centrally between four outcoupling gratings 4. The sensor fields are optically separated with the aid of structures 16 composed of light-absorbing material.

Figure 2:
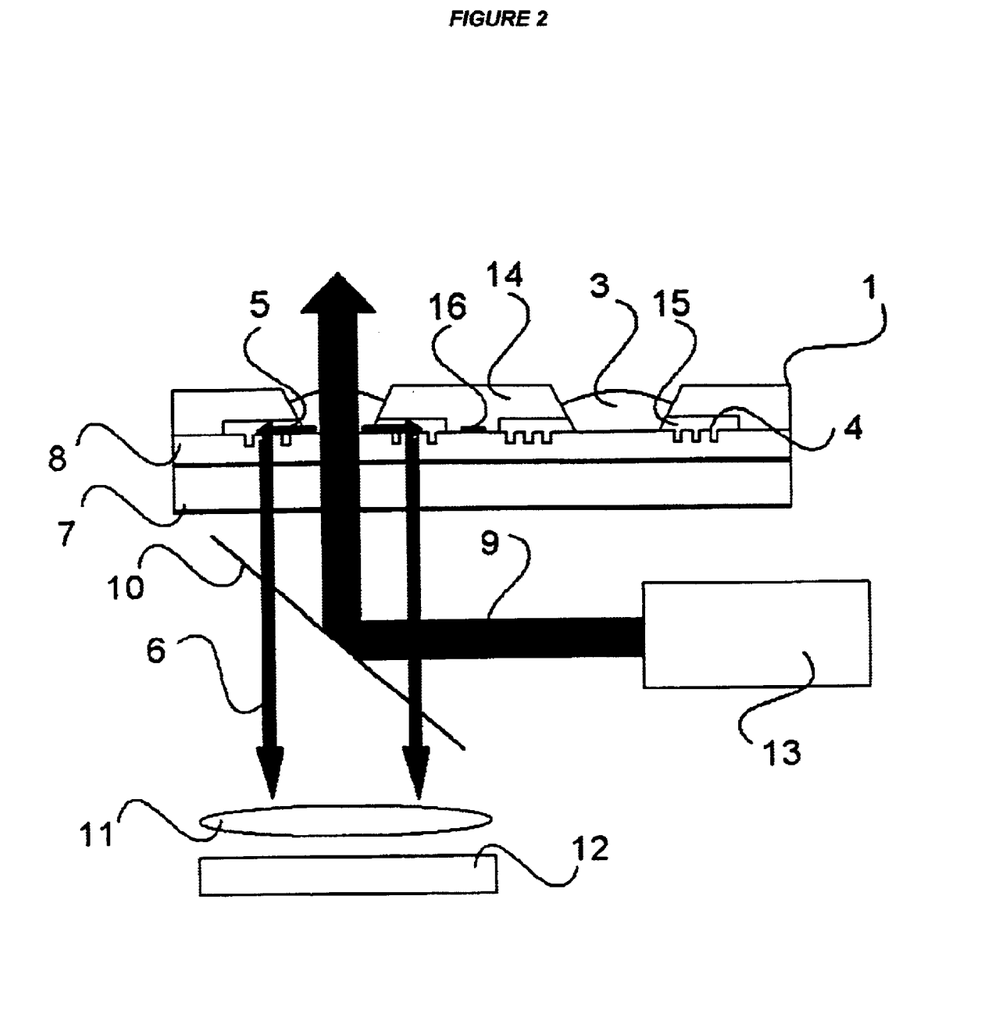
FIG. 2 illustrates a measuring device.

FIG. 2 illustrates a measuring device according to the invention. Here, the sensor platform 1 is designed as a microtiter plate and has sensor fields located between outcoupling gratings 4 for the luminescence radiation 5, 6. The analyte samples 3 are illuminated at right angles through a substrate 7 and a waveguiding layer 8 with excitation light beams 9. The luminescence radiation 5 penetrating in the immediate proximity into the waveguide 8 and propagating in the waveguide, is guided as discrete beams 6 via the outcoupling gratings 4 and a dichroic mirror filter 10 to imaging optics 11, and from there to a detection device 12 (CCD camera or photomultiplier). The excitation light beams 9 are fed to the analyte sample 3 via the reflecting surface of the dichroic mirror 10. The excitation light beams 9 originate from an excitation light source (laser) 13. The sample containers are designed as cutouts in a cover layer 14 which, outside optically transparent interlayers 15 provided in the immediate proximity of the coupling gratings 4, consists of light-absorbing material in order to avoid optical crosstalk between neighboring cutouts. In addition to an absorbing cover layer 14, it is possible for structures 16 composed of light-absorbing material (for example, chromium) also to be applied directly to the waveguiding layer, directly onto the sensor platform, designed as the microtiter plate 1, between the neighboring analyte cutouts, in order to prevent optical crosstalk from luminescence light 5 propagating in the waveguide 8.

The following example explains the invention in more detail.

EXAMPLE

The effectiveness of the excitation method in the volume of an analyte sample 3 is tested with the aid of a DNA hybridizing assay. The waveguide consists of Corning glass C7059 as substrate material 7 and $Ta_2O_5$ as waveguiding layer 8 (layer thickness 150 nm), and contains two outcoupling gratings 5 with a modulation transfer factor of approximately 10 nm and a grating period of 320 nm. The cutout for the analyte sample is located in the middle of the grating at a distance of 5 mm. In order to immobilize oligonucleotide detection elements, the waveguiding surface is silanized with 3-glycidoxypropyltrimethoxysilane in the liquid phase (ortho-xylene). The following oligonucleotide is covalently immobilized as a detection element on the functionalized silane layer with a typical occupation density of 10%. Amino-(C6bridging group)5'-CACAATTCCACACAAC-3'. The covalent bonding of the oligonucleotide is performed via the free amino group of the oligonucleotide and the epoxide group of the silane layer. Immobilization is performed with an oligonucleotide concentration of 0.1 mM oligonucleotide in 100 mM of bicarbonate buffer with a pH of 8.7.

Hybridization with an oligonucleotide which is complementary to the detection element and is fed for 3 minutes in continuous flow via a buffer solution is used for detection in a specific binding assay. The oligonucleotide used for detection is likewise marked at the 5'-end with the fluorescence dye Cy5. The sequence of the oligonucleotides used for detection is as follows: Cy5-5'-GTTGTGTGGAATTGTG-3'.

The complementary oligonucleotide is applied in increasing quantities from 0.5 to 500 $\mu$M, the sensor surface being regenerated with NaOH (10 mM) before each application.

The excitation surface in the analyte sample for the laser light with a wavelength of 633 nm is 0.5 mm$^2$, and the intensity of the excitation light is 2.4 mW. The sample container is illuminated from the substrate side at an angle of approximately 45° to the substrate normals. The direction of illumination likewise forms an angle of approximately 45° (in conjunction with virtually perpendicular outcoupling) to the direction of the fluorescence outcoupling light 6 at a coupling grating 5, and thus keeps the background signal of the measurement at a very low level (and Correspondingly low noise) owing to the opposite directions of excitation and emission and to the fact that the excitation and emission sites are separated from one another in space.

In order to determine the optical response signal, the ratio of the net signal (maximum sensor signal, minus background signal in the buffer) to the background noise is given as a function of the concentration. The measurement result is represented in the following table:

TABLE

| Concentration (pM): | 0.5 | 1 | 5 | 10 | 25 | 50 | 500 |
|---|---|---|---|---|---|---|---|
| Signal:noise: | 1.5 | 3.5 | 11.7 | 53.5 | 58.0 | 118.8 | 225.1 |

The standard deviations of the signal noise values from three sequentially performed, concentration-dependent measurement series is ≦4%.

What is claimed is:

1. A method for exciting and determining a luminescence in an analyte sample which is located in contact with a waveguiding layer of an optical layer waveguide, said method comprising:
   generating the luminescence by non-evanescent excitation in a volume of the analyte sample as luminescence radiation;
   guiding the luminescence radiation generated in an immediate proximity of a surface of the waveguiding layer to a measuring device after the luminescence radiation penetrates the waveguiding layer; and
   measuring the luminescence radiation with the measuring device.

2. The method as claimed in claim 1, wherein said generating of the luminescence radiation comprises generating the luminescence radiation one of electrically, chemically, and by optical excitation of radiation.

3. The method as claimed in claim 2, wherein said generating of the luminescence radiation comprises generating the luminescence radiation by the optical excitation of radiation, the excitation radiation of the optical excitation of radiation being directed onto the analyte sample from a side of the waveguiding layer opposite to a side of the waveguiding layer where said guiding of the luminescence radiation occurs by a planar waveguide.

4. The method as claimed in claim 1, wherein the optical layer waveguide is a planar waveguide with outcoupling elements for the luminescence radiation.

5. The method as claimed in claim 4, wherein the optical layer waveguide contains one or more diffractive elements as the outcoupling elements for coupling out the luminescence radiation, and the analyte sample is arranged one of upstream of and between at least two of the outcoupling elements.

6. A method for exciting and determining a luminescence in an analyte sample which is located in contact with at least two waveguides with diffractive outcoupling elements of a sensor platform which has a one-dimensional arrangement or a two-dimensional arrangement of the at least two waveguides, said method comprising;
   generating the luminescence by non-evanescent excitation in a volume of the analyte sample as luminescence radiation;
   guiding the luminescence radiation generated in an immediate proximity of a surface of waveguiding layers of the at least two waveguides to a measuring device after the luminescence radiation penetrates the waveguiding layer; and
   measuring the luminescence radiation with the measuring device.

7. The method as claimed in claim 6, wherein the sensor platform is covered with a second layer which contains cutouts for holding the analyte sample in a region of the guided luminescence radiation.

8. A device for measuring luminescence generated in an analyte sample by excitation radiation, said device comprising:
   at least one optical layer waveguide comprising a transparent substrate and a waveguiding layer, said waveguiding layer adapted to have an analyte sample located in contact therewith;
   one of an electric energy source operable to generate an electric field, said electric energy source having electrodes, and an optical energy source operable to emit excitation radiation, wherein said electrodes of said electric energy source are located in direct contact with the analyte sample, and the excitation radiation of said optical energy source is directed directly onto the analyte sample at an inclined angle or a right angle, or a reservoir containing a chemical which excites a chemiluminescence in contact with the analyte sample; and
   an optoelectronic detection unit operable to measure luminescence radiation generated by the action of the electric field or the excitation radiation.

9. The device as claimed in claim 8, wherein said at least one optical layer waveguide is a plurality of optical layer waveguides, said plurality of optical layer waveguides being planar waveguides which have at least one outcoupling element for coupling out the luminescence radiation.

10. A sensor platform comprising:
    a planar optical layer waveguide comprising:
      a transparent substrate,
      a waveguiding layer,
      at least one outcoupling element operable to couple out excitation radiation, and
      a tight sealing layer located on said waveguiding layer, said tight sealing layer having, at least in a subregion of the excitation radiation, a cutout having an open top or a closed top and connected to an inflow channel and outflow channel, for an analytical sample, said cutout having a depth at least corresponding to a depth of penetration of an evanescent field of luminescence light guided in said planar optical layer waveguide, wherein
    said tight sealing layer comprises a material which, at least on a bearing surface at least in the depth of penetration of the evanescent field of the luminescence light guided in said planar optical layer waveguide, is transparent to the luminescence light, and
    said at least one outcoupling element is completely covered by said material of said tight sealing layer at least in an outcoupling region of the luminescence radiation.

* * * * *